United States Patent
Sheidaei et al.

(10) Patent No.: US 12,310,635 B2
(45) Date of Patent: May 27, 2025

(54) TUNABLE STIFFNESS BONE ROD

(71) Applicant: Iowa State University Research Foundation, Inc., Ames, IA (US)

(72) Inventors: Azadeh Sheidaei, Ames, IA (US); Mohammad Saber Hashemi, Ames, IA (US); Karl Kraus, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 17/304,282

(22) Filed: Jun. 17, 2021

(65) Prior Publication Data
US 2021/0393300 A1    Dec. 23, 2021

Related U.S. Application Data (60) Provisional application No. 62/705,272, filed on Jun. 19, 2020.

(51) Int. Cl.
*A61B 17/72* (2006.01)

(52) U.S. Cl.
CPC .................... *A61B 17/72* (2013.01)

(58) Field of Classification Search
CPC ........ A61B 17/72–7291; A61B 17/7019–7031
USPC .................................................. 606/254–258
See application file for complete search history.

(56) References Cited

U.S. PATENT DOCUMENTS

| | | | | |
|---|---|---|---|---|
| 2004/0215191 A1* | 10/2004 | Kitchen | ............ | A61B 17/7029 606/264 |
| 2007/0191832 A1* | 8/2007 | Trieu | ................. | A61B 17/7049 606/86 A |
| 2009/0093846 A1* | 4/2009 | Hestad | ............... | A61B 17/7008 606/255 |
| 2019/0282280 A1 | 9/2019 | Harshman et al. | | |

FOREIGN PATENT DOCUMENTS

| AU | 2020201392 A1 | 3/2020 |
|---|---|---|
| CN | 106983551 A | 7/2017 |

OTHER PUBLICATIONS

Bottlang et al., "Far Cortical Locking Can Reduce Stiffness of Locked Plating Constructs While Retaining Construct Strength", The Journal of Bone & Joint Surgery, vol. 91-A, No. 8, pp. 1985-1994, Aug. 2009.

Huang et al., "Stiffness and strength design of composite bone plates", Composites Science and Technology, vol. 65, pp. 73-85, 2005.

(Continued)

*Primary Examiner* — Nicholas J Plionis
(74) *Attorney, Agent, or Firm* — McKee, Voorhees & Sease, PLC (57) ABSTRACT

A tunable stiffness bone rod promotes the healing of fractured bones, such as tibia bones. The tunable stiffness bone rod includes a hexagonal shape that has variable levels of stiffness upon application of an axial force. The axial force will begin a low stiffness movement of the bone rod until a threshold is met. Upon reaching the threshold, the stiffness of the bone rod increases to lessen additional longitudinal movement caused by the axial force on the bone rod.

16 Claims, 11 Drawing Sheets

(56) References Cited

OTHER PUBLICATIONS

Kim et al., "Finite element analysis using interfragmentary strain theory for the fracture healing process to which composite bone plates are applied", Composite Structures, vol. 93, pp. 2953-2962, 2011.

Mehboob et al., "Effect of initial micro-movement of a fracture gap fastened by composite prosthesis on bone healing", Composite Structures, vol. 226, 111213, pp. 1-8, 2019.

Mehboob et al., "Effect of structural stiffness of composite bone plate-scaffold assembly on tibial fracture with large fracture gap", Composite Structures, vol. 124, pp. 327-336, 2015.

Mehboob et al., "Finite element analysis of tissue differentiation process of a tibia with various fracture configurations when a composite intramedullary rod was applied", Composites Science and Technology, vol. 80, pp. 55-65, 2013.

Müller et al., "A Novel Shape Memory Plate Osteosynthesis for Noninvasive Modulation of Fixation Stiffness in a Rabbit Tibia Osteotomy Model", BioMed Research International, vol. 2015, Article ID 652940, pp. 1-8, http://dx.doi.org/10.1155/2015/652940, 2015.

Nourisa et al., "Biomechanical evaluation of intramedullary nail and bone plate for the fixation of distal metaphyseal fractures", Journal of the Mechanical Behavior of Biomedical Materials, vol. 56, pp. 34-44, 2016.

Nourisa et al., "The Effects of Bone Screw Configurations on the Interfragmentary Movement in a Long Bone Fixed by a Limited Contact Locking Compression Plate", J. Biomedical Science and Engineering, vol. 8, pp. 590-600, http://dx.doi.org/10.4236/jbise.2015.89055, 2015.

Son et al., "The simulation of bone healing process of fractured tibia applied with composite bone plates according to the diaphyseal oblique angle and plate modulus", Composites: Part B, vol. 45, pp. 1325-1335, 2013.

Tonino et., "Protection From Stress in Bone and Its Effects", The Journal of Bone and Joint Surgery, vol. 58-B, No. 1, pp. 107-113, Feb. 1976.

Yu et al., "Impact of mechanical stretch on the cell behaviors of bone and surrounding tissues", Journal of Tissue Engineering, vol. 7, pp. 1-24, DOI: 10.1177/2041731415618342, 2016.

Maggi, Alessandro et al., Three-dimensional nano-architected scaffolds with tunable stiffness for efficient bone tissue growth, Acta Biomaterial, vol. 63, Nov. 2017.

* cited by examiner

TUNABLE STIFFNESS BONE ROD

CROSS REFERENCE TO RELATED APPLICATIONS

This application claims priority under 35 U.S.C. § 119 to provisional patent application U.S. Ser. No. 62/705,272, filed Jun. 19, 2020. The provisional patent application is herein incorporated by reference in its entirety, including without limitation, the specification, claims, and abstract, as well as any figures, tables, appendices, or drawings thereof.

FIELD OF THE INVENTION

The invention relates generally to an apparatus and corresponding method of use healing of fractured bones. More particularly, but not exclusively, the invention relates to a tunable stiffness bone rod to aid in the healing of long fractured bones.

BACKGROUND OF THE INVENTION

Figure 1A:
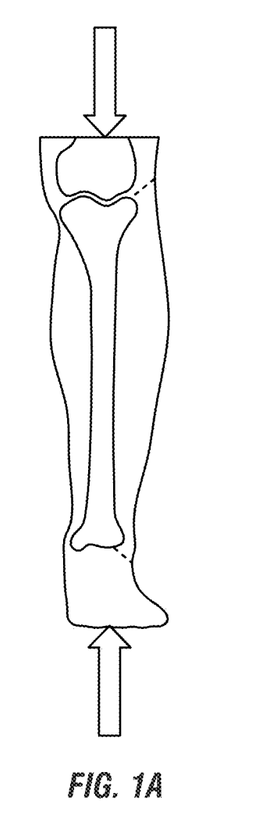
FIG. 1A is a view of a tibia bone under axial loading.
Figure 1B:
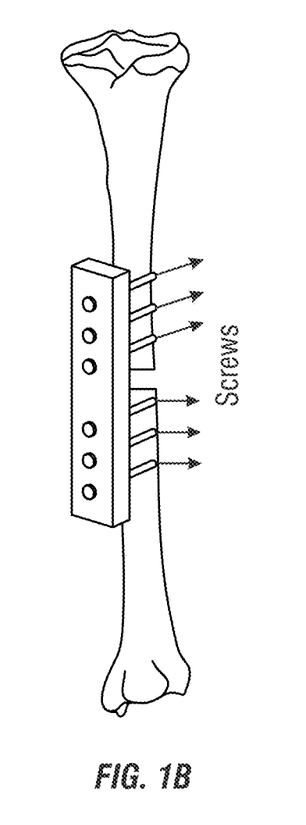
FIG. 1B is a depiction of a prior art bone plate fixing fractured bone parts with screws.
Figure 1C:
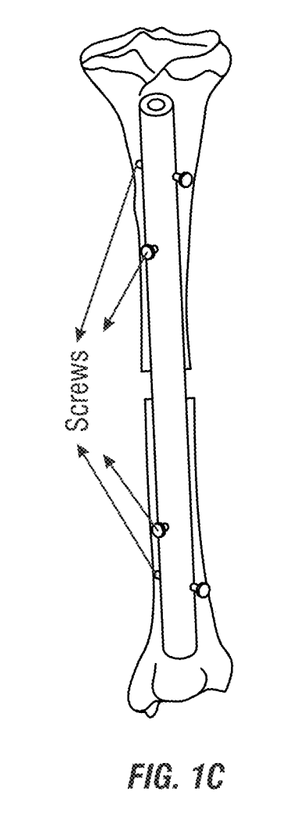
FIG. 1C is a depiction of a bone rod inserted inside the bone and fixing the fractured bone parts with screws in different planes.

Fractures of the long bones such as femur, tibia, fibula, humerus, radius, and ulna can be fixed using a bone plate (FIG. 1B) or intramedullary rod (FIG. 1C). The bone plate is attached to the outer surface of the bone while the bone rod is inserted into the hollow canal of the long bones. Upon applying axial load on the bone (see, e.g., FIG. 1B), an off-axial force is exerted on the bone-plate, and the whole assembly is rotated. This rotation causes the non-uniform formation of the callus that results in the non-uniform formation of the bone. Consequently, it makes bone fracture of the same site more likely in a future accident. Bone rods solve this problem partially since the bone rod and the bone are co-axial, preventing the broken bone from rotating. Following the bone fracture, callus forms in the fracture site and gradually becomes bone. The quality of this newly formed bone highly depends on the strain level during the walking, and it should be between 8-10%. Any deformation out of this range results in poor healing of the bone.

Existing bone rods are circular shafts with constant stiffness, and they do not stop the deformation under excess load to prevent higher strain on the fracture site, nor do they have the initial flexibility for optimum bone growth. Therefore, a tunable stiffness bone rod is needed to control and stop the deformation. There are few examples of flexible bone rods, but in all these designs, a mechanism or extra parts have been added, such as spring and loose/sliding screws for adding flexibility. These designs are not patient-specific, and they are unable to control the amount of strain.

In addition to the stiffness tunability of the bone fixator, its stiffness plays an essential role in the healing process. In the surgery, patients with fractures are treated using bone fixators made of stainless-steel, Cr—Co, and Ti alloys. The stiffnesses of these metals are between 110-220 GPa, which are much higher than that of human cortical bone ~20 GPa. As a result, the majority of the load is carried by the fixator rather than the underlying bone. Subsequently, callus formation, ossification, and bone union at the fractured part are hindered after the implant operation, and the whole bone structure, not only at the fractured part, becomes osteoporosis. The bone mass can be decreased by 20%, and in some cases, the bone re-fracture due to stress concentration around the bone screws. These phenomena are widely recognized as the "stress shielding" effect, which is the main drawback of the use of metal bone fixators. A bone fixator with stiffness close to the bone or lower is needed to prevent stress-shielding and to prevent osteoporosis in patients.

Thus, there exists a need in the art for an apparatus which overcomes the deficiencies in the art, including a bone rod with a tunable stiffness that overcomes the issues presented while also encouraging the healing of a fractured bone.

SUMMARY OF THE INVENTION

The following objects, features, advantages, aspects, and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

It is a primary object, feature, and/or advantage of the present invention to improve on or overcome the deficiencies in the art.

It is a further object, feature, and/or advantage to promote the healing of a fractured bone in a controlled manner.

It is still yet a further object, feature, and/or advantage to address the common shortcomings of existing bone rods in the healing of long fractured bones.

The bone rod disclosed herein can be used in a wide variety of applications. For example, while the applications are directed towards fractured tibias, it should be appreciated that the bone rod could be used with other fractures as well.

At least one embodiment disclosed herein comprises a distinct aesthetic appearance. Ornamental aspects included in such an embodiment can help capture a consumer's attention and/or identify a source of origin of a product being sold. Said ornamental aspects will not impede functionality of the present invention.

Methods can be practiced which facilitate use, manufacture, assembly, maintenance, and repair of the bone rod which accomplish some or all of the previously stated objectives.

According to some aspects of the present disclosure, a tunable bone rod comprises
an elongated rod, and a tunable stiffness unit positioned axially along the longitudinal length of the elongated rod, said tunable stiffness unit comprising a stiffness block comprising an upper flex member and a lower flex member separated by a gap, and a support arm connected to the upper and lower flex members, wherein said upper and lower flex members movable to contact one another under axial load.

According to at least some of the aspects and/or embodiments, said tunable stiffness unit further comprising a plurality of upper of lower flex members, wherein each upper flex member is associated with a lower flex member via a separate support arm and flexibly separable by a gap.

According to at least some of the aspects and/or embodiments, the upper and lower flex members and the support arm comprise a hexagonal shape.

According to at least some of the aspects and/or embodiments, the hexagonal shape comprises an irregular hexagon.

According to at least some of the aspects and/or embodiments, the stiffness unit further comprises an upper and lower stiffness block positioned in axial relationship along the length of the elongated rod.

According to at least some of the aspects and/or embodiments, the stiffness unit comprises a plurality of radially spaced stiffness blocks used together.

According to at least some of the aspects and/or embodiments, the plurality of radially spaced stiffness blocks comprises three stiffness blocks used together.

According to at least some of the aspects and/or embodiments, the tunable bone rod comprises stainless steel.

According to at least some of the aspects and/or embodiments, the stiffness unit deforms upon application of axial force with low stiffness, and becomes stiffer when the gap between the upper member and lower member closes.

Additional aspects and/or embodiments include a tunable stiffness block for use in aiding the healing of a bone fracture, comprising an upper block body, a lower block body, and a support arm connecting the upper and lower block body to form a hexagonal cavity between the upper and lower block bodies, wherein a gap is formed between the upper and lower block bodies.

According to at least some of the aspects and/or embodiments, the support arm flexes to close the gap between the upper and lower block bodies under an axial load.

According to at least some of the aspects and/or embodiments, the upper and lower block bodies include upper and lower flanges at distally opposite ends of the tunable stiffness block.

According to at least some of the aspects and/or embodiments, the upper and lower block bodies are substantially symmetrical.

According to at least some of the aspects and/or embodiments, the hexagonal cavity comprises an irregular hexagon shape.

Additional aspects and/or embodiments include a tunable stiffness unit for use in aiding the healing of a bone fracture, comprising, a plurality of tunable stiffness blocks each comprising an upper block body, a lower block body, a support arm connecting the upper and lower block body to form a hexagonal cavity between the upper and lower block bodies, wherein a gap is formed between the upper and lower block bodies; wherein the plurality of tunable stiffness units are oriented longitudinally and/or radially.

According to at least some of the aspects and/or embodiments, the plurality of tunable stiffness blocks comprises two stiffness blocks stacked longitudinally.

According to at least some of the aspects and/or embodiments, the plurality of tunable stiffness blocks comprises three sets of two longitudinally stacked stiffness blocks radially spaced.

According to at least some of the aspects and/or embodiments, the support arm of the stiffness blocks flexes to close the gap between the upper and lower block bodies under an axial load.

According to at least some of the aspects and/or embodiments, the stiffness block comprises stainless steel.

According to at least some of the aspects and/or embodiments, the gap is sized to be approximately 9% of a bone fracture gap.

These and/or other objects, features, advantages, aspects, and/or embodiments will become apparent to those skilled in the art after reviewing the following brief and detailed descriptions of the drawings.

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

BRIEF DESCRIPTION OF THE DRAWINGS

Several embodiments in which the invention can be practiced are illustrated and described in detail, wherein like reference characters represent like components throughout the several views. The drawings are presented for exemplary purposes and may not be to scale unless otherwise indicated.

An artisan of ordinary skill need not view, within isolated figure(s), the near infinite number of distinct permutations of features described in the following detailed description to facilitate an understanding of the invention.

DETAILED DESCRIPTION OF THE INVENTION

The present disclosure is not to be limited to that described herein. Mechanical, electrical, chemical, procedural, and/or other changes can be made without departing from the spirit and scope of the invention. No features shown or described are essential to permit basic operation of the invention unless otherwise indicated.

Unless defined otherwise, all technical and scientific terms used above have the same meaning as commonly understood by one of ordinary skill in the art to which embodiments of the invention pertain.

The terms "a," "an," and "the" include both singular and plural referents.

The term "or" is synonymous with "and/or" and means any one member or combination of members of a particular list.

The terms "invention" or "present invention" are not intended to refer to any single embodiment of the particular invention but encompass all possible embodiments as described in the specification and the claims.

The term "about" as used herein refer to slight variations in numerical quantities with respect to any quantifiable variable. Inadvertent error can occur, for example, through use of typical measuring techniques or equipment or from differences in the manufacture, source, or purity of components.

The term "substantially" refers to a great or significant extent. "Substantially" can thus refer to a plurality, majority, and/or a supermajority of said quantifiable variable, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

The "scope" of the invention is defined by the appended claims, along with the full scope of equivalents to which such claims are entitled. The scope of the invention is further qualified as including any possible modification to any of the aspects and/or embodiments disclosed herein which would result in other embodiments, combinations, subcombinations, or the like that would be obvious to those skilled in the art.

The invention is directed generally towards a tunable stiffness bone rod 10, which improves upon and addresses common shortcomings of existing bone rods in the healing of long fractured bones, such as a tibia. As noted herein, and shown in FIGS. 1A-1C, fractured bones undergo axial forces, such as during walking or movement. This is shown generally by the arrows in FIG. 1A. The common deficiencies of existing bone fixations, which are illustrative of the devices shown in prior art devices of FIGS. 1B and 1C, of existing bone fixations are high stiffness, thereby negligible flexibility in deformation for best bone growth results, and stress-shielding effect.

As will be understood, the novel design and configuration of the tunable stiffness bone rod 10 according to the aspects and embodiments disclosed herein provides the surgeons with ready-for-3D-printing patient-specific designs, optimized to have desired force-displacement response with a stopping mechanism for preventing further deformation in higher than usual loads such as falling.

Figure 2:
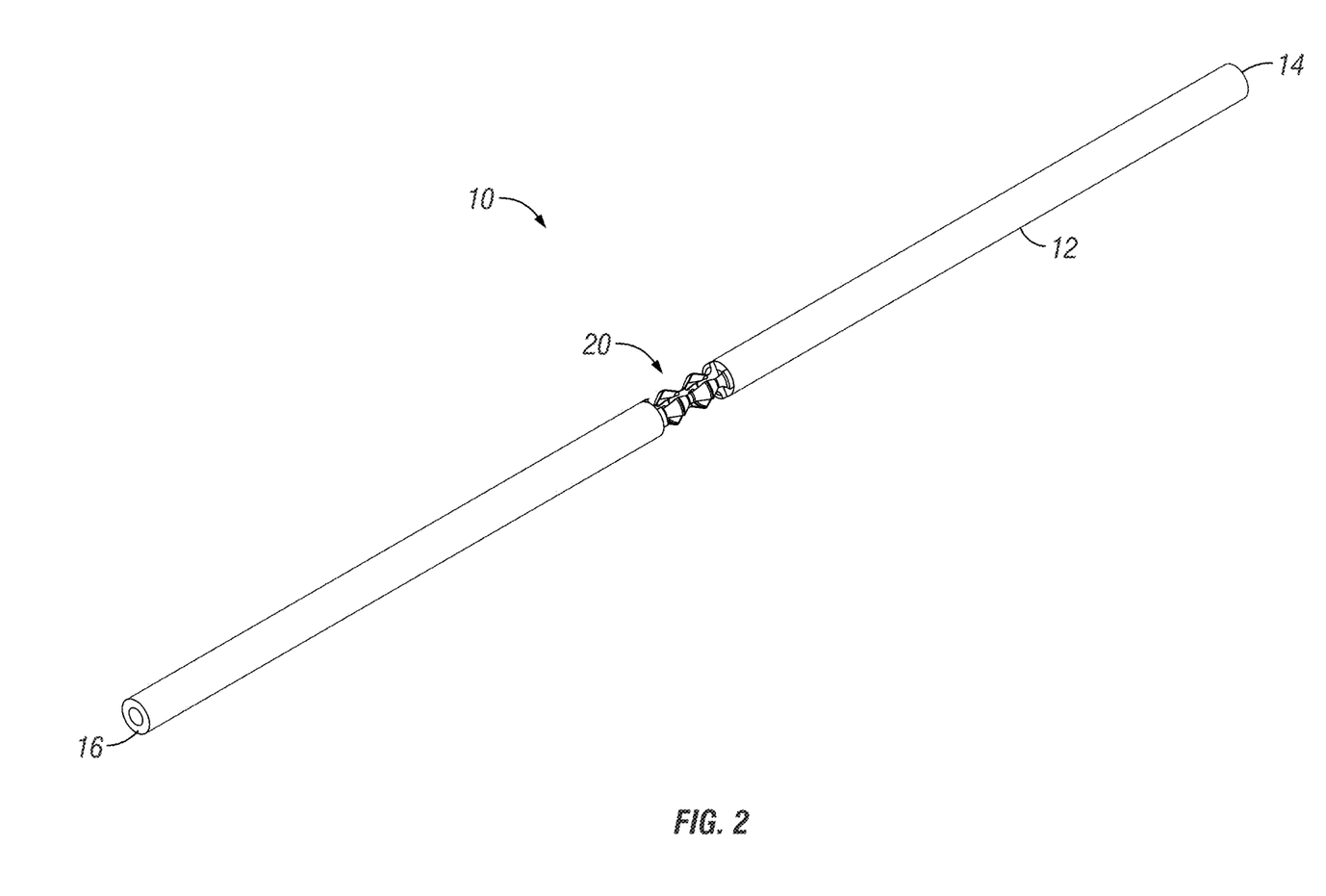
FIG. 2 is a perspective view of bone rod for use in healing a fractured bone.

Therefore, FIG. 2 provides an illustrative tunable stiffness bone rod 10 according to aspects of the invention. The bone rod 10 includes a generally elongated rod portion 12, which may include upper and lower portions. The rod 12 includes a first end 14 and an opposite second end 16. As will be understood (see, e.g., FIG. 7), the bone rod 10 will be positioned in a fractured bone 18. Thus, the first and second ends 14, 16, can be referred to according to the orientation of the bone 18, such as related to upper and lower portions. Still further, as will be understood, the bone rod 10 can be affixed to the bone 18 in a number of ways, including, but not limited to, screws 19 or other mechanical fasteners. Screws, nuts, bolts, pins, rivets, staples, washers, grommets, latches (including pawls), ratchets, clamps, clasps, flanges, ties, adhesives, welds, any other known fastening mechanisms, or any combination thereof may be used to facilitate fastening. Still further, the fasteners could be general fasteners, such as keys, pins, retaining rings, etc., or they could be threaded fasteners, such as bolts, screws, studs, setscrews, etc.

Positioned axially along the longitudinal length of the elongated rod 12 is a tunable stiffness unit 20. As will be understood, the tunable stiffness unit 20 allows for at least some axial movement of the tunable stiffness bone rod 10. It is this longitudinal/axial movement that allows for the bone rod to encourage healing of the fractured bone in a way that improves on the art.

Figure 3:
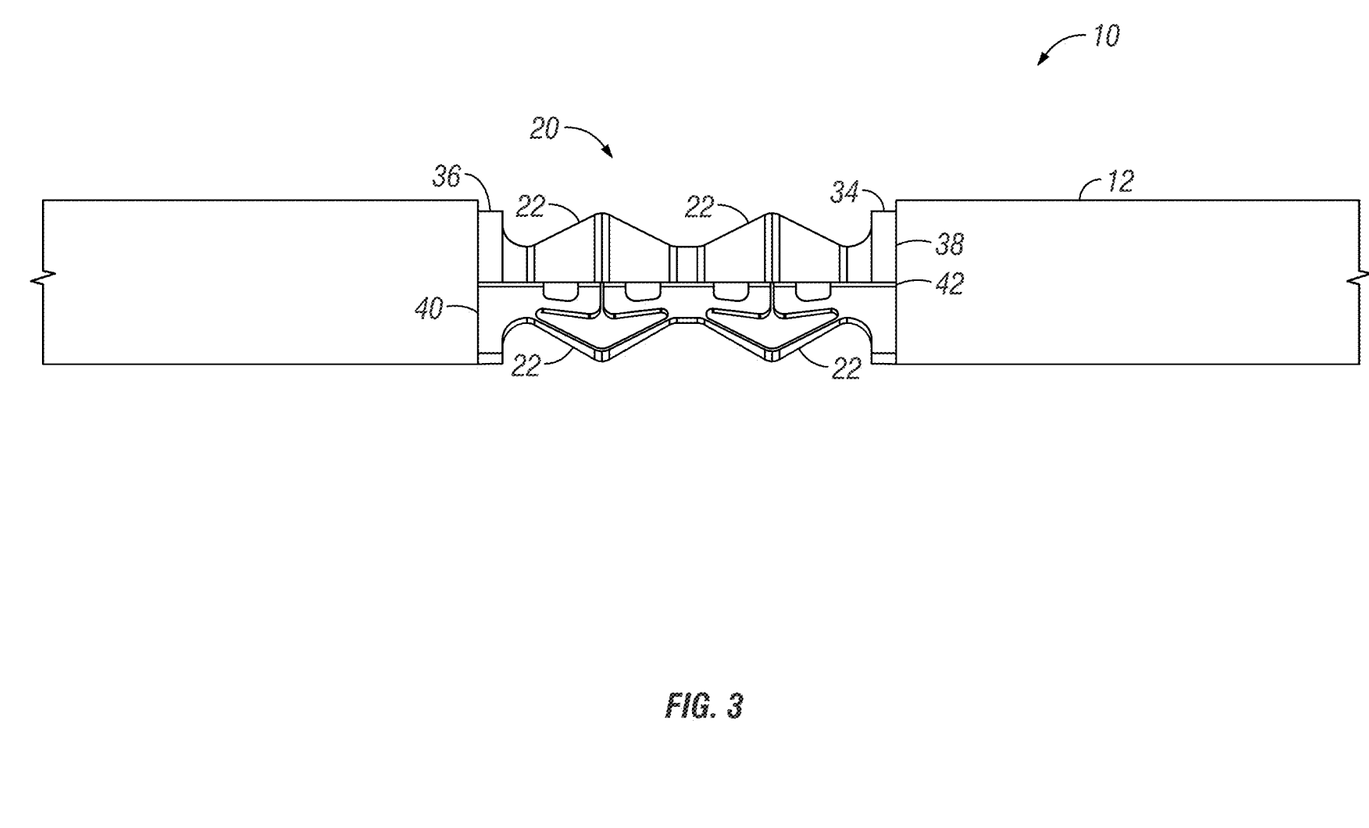
FIG. 3 is an enlarged view of a tunable stiffness unit for use with a bone rod such as shown in FIG. 2, according to aspects of the present disclosure.
Figure 4:
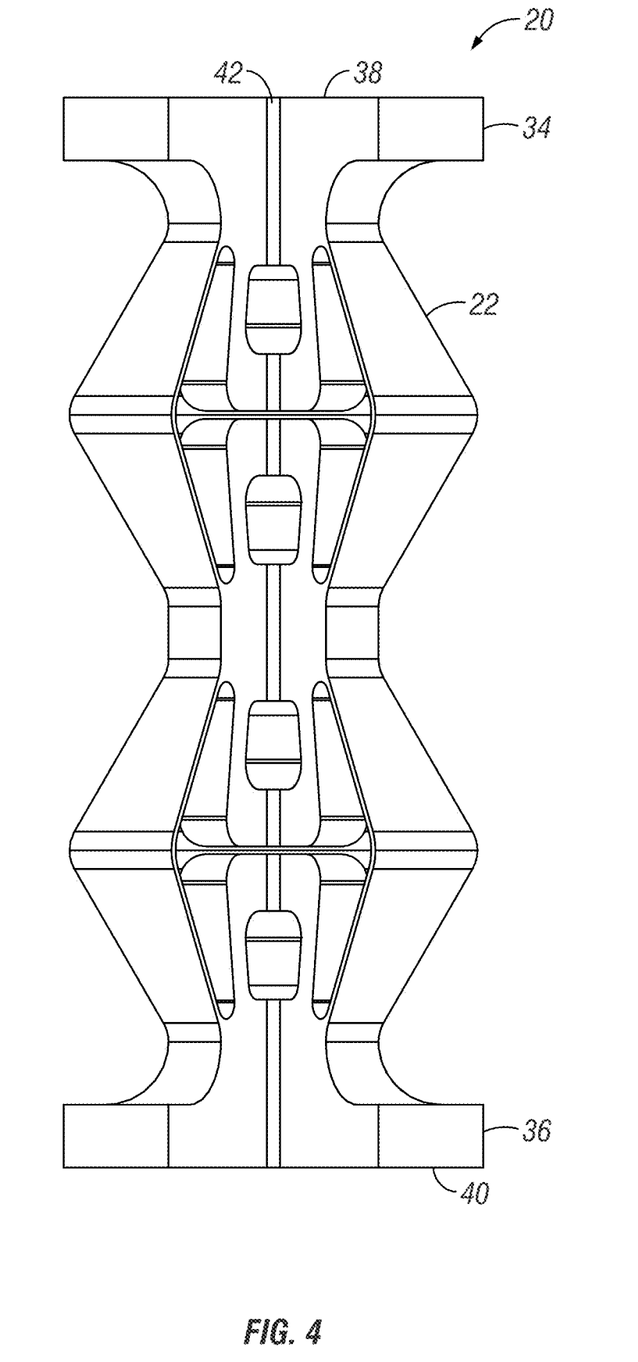
FIG. 4 is another enlarged view of a tunable stiffness unit.

FIGS. 3 and 4 are enlarged views of the tunable stiffness units 20 positioned with the elongated rod 12 (FIG. 3) and isolated (FIG. 4). As will be understood, the stiffness units 20 comprise a plurality of stiffness blocks 22. As shown in the figures, the stiffness blocks can be stacked axially such that two stiffness blocks are stacked together in the longitudinal length of the rod. In addition, three clusters of the stacked stiffness blocks 22 can be radially positioned around the common axis 42 of the bone rod 10. In the figures, three clusters of stacked stiffness blocks 22 are radially positioned around the axis 42 of the rod to form the stiffness unit 20. However, it should be appreciated that more or less blocks, stacks, and/or clusters could be utilized as part of the stiffness unit 20 to be combined with a rod 12 to form a tunable stiffness bone rod 10.

Additional aspects of the stiffness unit include upper and lower flange portions 42-36 at opposite longitudinal ends of the unit 20. The flanges for connection interfaces 38, 40 that connect the stiffness unit 20 to the elongated bone rod 12. The stiffness unit may be connected to the portions of the rod 12 in a number of ways, including but not limited to, adhesives, welding, mechanical fasteners, or the like. In addition, as will be appreciated, the bone rod 10, including the elongated rod portions 12 and the stiffness unit 20, could form one integral piece of material, such as made by additive manufacturing (e.g., 3D printing or the like).

Figure 5:
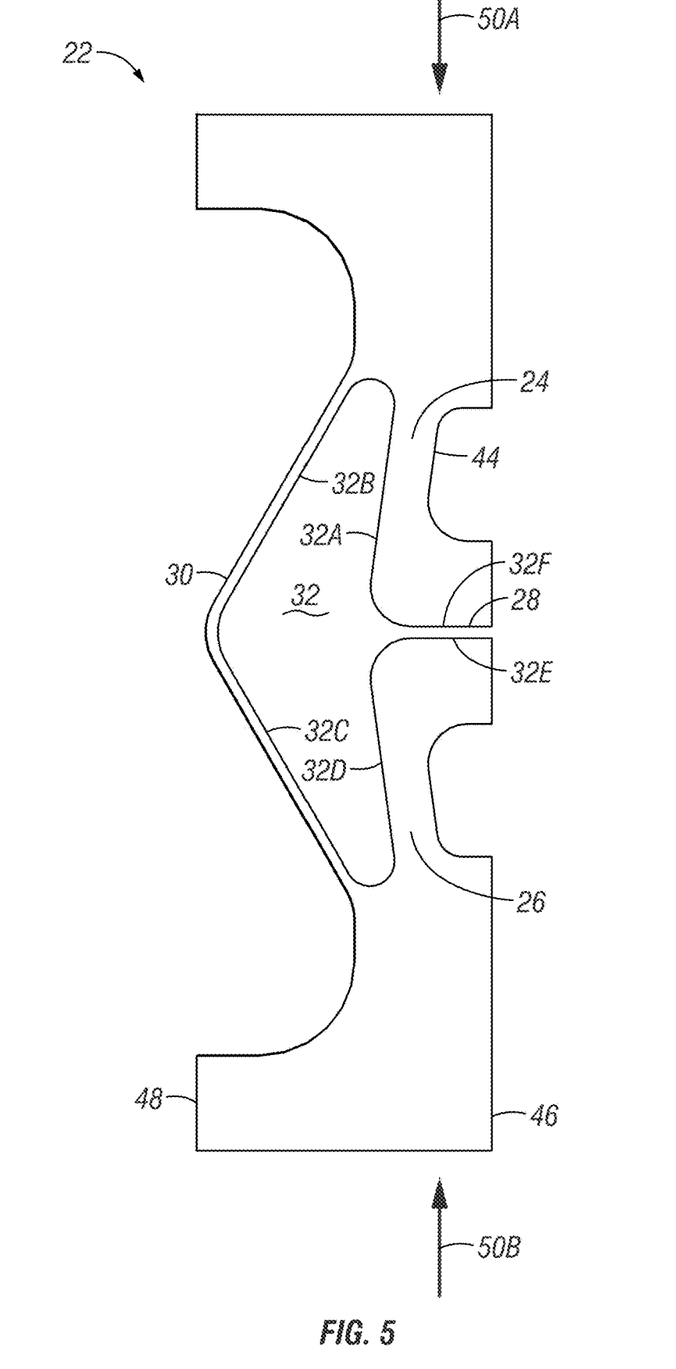
FIG. 5 is a view of a tunable stiffness block according to aspects of the disclosure.
Figure 6:
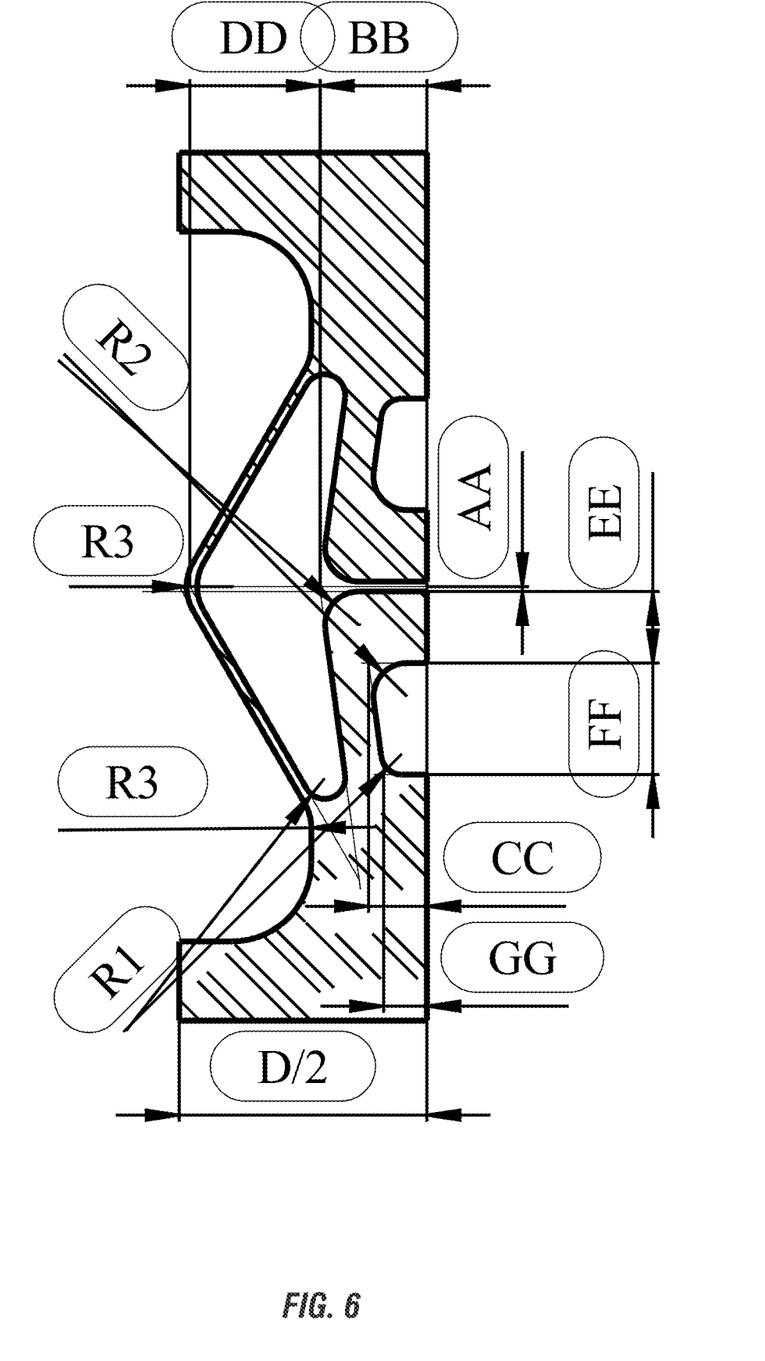
FIG. 6 is an annotated view of the tunable stiffness block of FIG. 5.

FIGS. 5-6 show enlarged side views of a stiffness block 22, such as those that make up the stacks and clusters of the stiffness units 20. For purposes of illustration, a stiffness block 22 as shown in FIG. 5 includes generally an upper portion and a lower portion, such as is oriented on the page. While the block 22 includes upper and lower flange portions, the block may take various configurations thereat, such as based upon stacking or other uses.

In general, the block 22 comprises an upper flex or body member 24, a lower flex or body member 26, and a support arm 30 connecting the upper and lower body members 24, 26. The upper and lower body members are separated by a gap 28 therebetween. As will be understood, the gap 28 is included to allow for some axial movement of the stiffness block 22 due to an axial force or pressure. The support arm 30 is provided to control the flexing and movement of the upper and lower flex/body members 24, 26, which will control at least some axial movement of the stiffness block 22. As will be understood, the supporting flex arm 30 will provide a controlled movement of the upper and lower body members 24, 26 under axial load (see, e.g., the arrows 50A, 50B in FIG. 5) until such time that the gap 28 is closed and the upper and lower members contact one another. At this point, the touching upper and lower members would control any axial movement (e.g., flexing) of the stiffness unit that may be caused by the axial load.

It will be noted that the upper member 24, lower member 26, and support arm 30 generally form a hexagonal shape interior 32. This is formed by the edges 32A of the upper member, 32B of the support arm, 32C of the support arm, 32D of the lower member, 32E of the lower member, and 32F of the upper member. Thus, the shape may be referred to as an irregular hexagonal shape. The shape 32 provides additional support for the stiffness block, such as by controlling the movement and flexing of the block to control movement during load on the stiffness block, which again, encourages improved healing of a fractured one.

Still additional components of the stiffness block include and interior face 46 and an exterior face 48. Along the interior face 46 are cavities 44, one each on the upper member 24 and the lower member 26. The cavities provide additional flex zones for the stiffness block 22.

The stiffness blocks 22 may comprise stainless steel or titanium. In addition, it should be appreciated that the elongated rod portions 12 may also comprise a similar material, such as stainless steel when it is used for the stiffness unit.

The stiffness block 22 and corresponding stiffness unit 20 has a bilinear elastic moduli. Referring back to the stiffness unit 20 comprising the stiffness blocks 22, upon application of an axial force on the unit, first, it deforms with low stiffness, and it becomes stiffer when the embedded gap 28 gets closed. The surrounding arms 30 are responsible for the soft mechanical response, and the cylindrical upper and lower parts 24, 26 in the middle acting as a mechanical fuse protect the arms from further deformation and cause more resistance to load, resulting in higher stiffness and slowing down the deformation. The 30 degrees inclinations of surrounding arms provide more flexibility compared to the case with straight arms.

Figure 11:
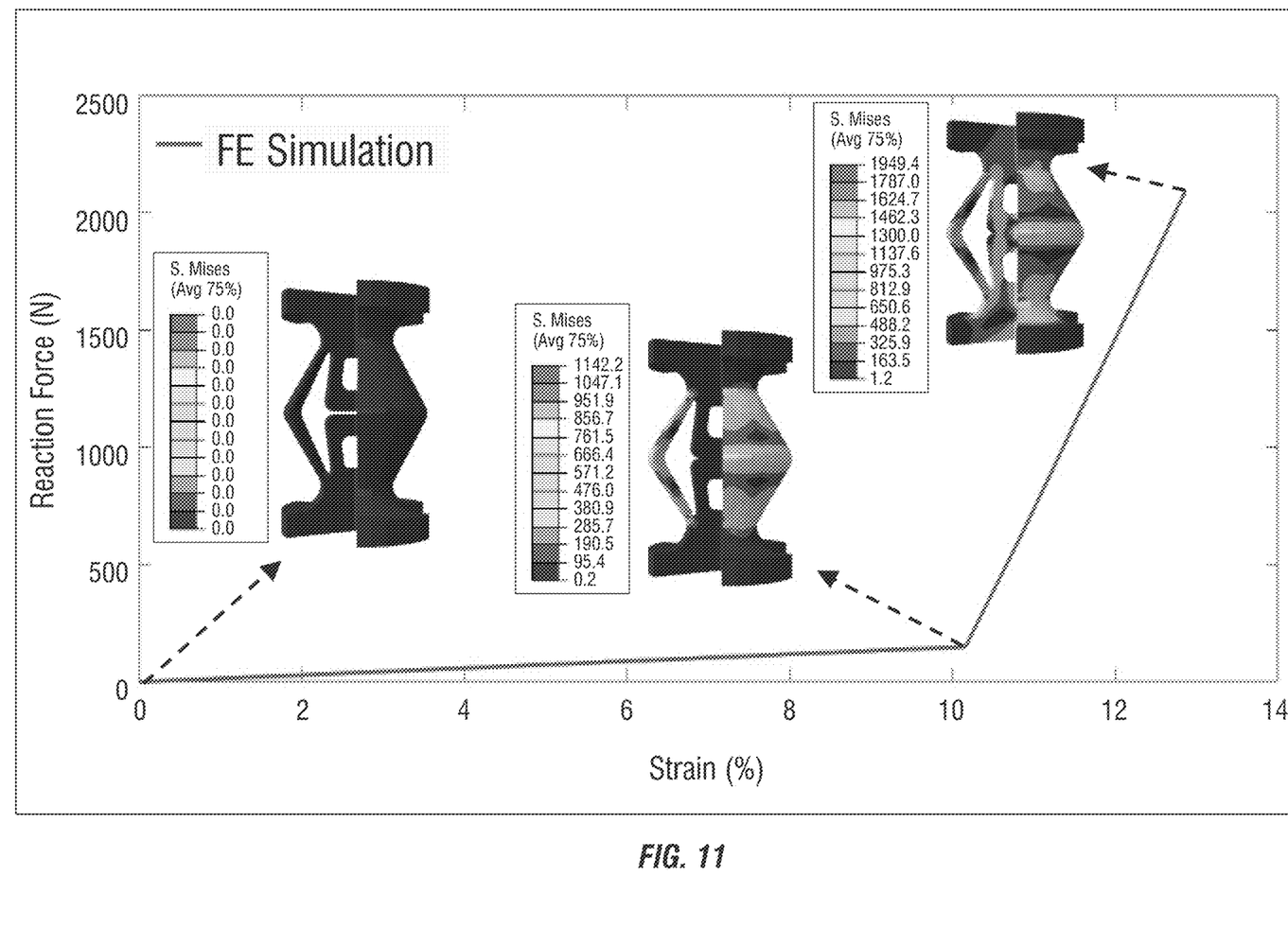
FIG. 11 is a graph showing compressive force vs. axial strain of a 3D model with contour plots of Mises stress associated with different stages of loading.

In order to link the mechanical properties to a set of quantifiable parameters, the geometry of such a design consisting of one hexagonal cell 32 must have been uniquely expressed by some parameters or measures. Except "D/2", which is essentially the bone rod radius constrained by the fractured bone size, they are manifested by ten parameters of a 2D sketch illustrated in FIG. 6. The radii of curved edges (R1, R2, R3) provide the block 22 with smooth stress flow to minimize stress concentration in those areas. The number of variables was defined such that there would be enough room for design flexibility to achieve different mechanical responses given the building material properties. As the material should remain elastic due to cyclic loadings imposed on the bone rod, a linear curve was expected before the gap closure. The contact incident would result in a much stiffer response compared with the mechanical response before the gap closure. As a result, the desired force-displacement curve is bilinear, the first segment with a low slope (low stiffness) and the second one as close as possible to a vertical line (very high stiffness). This change is shown in FIG. 11 curve with additional visualization of FE results (contour plots of Mises stress in a 3D model).

While FIGS. 5 and 6 show 2D sketches for a stiffness block 22, it is to be appreciated that the end product be 3D (see, e.g., FIGS. 2-4). It was determined that a single stiffness block such as the model of FIG. 5 revolved around a vertical symmetry axis, which resulted in a part with just one hexagonal cell could not reach the desired results. Therefore, other designs were optimized with more than one hexagonal cell. Having more cells require lower displacement in one cell since the total displacement is the sum of the displacements in all cells. As a result, the gap inside each cell could be narrowed accordingly.

Therefore, as shown in FIGS. 2-4, 7, and 8A-8C, a partially revolved design for the stiffness unit 20 was developed. The result may be referred to as a partially revolved design, or a clustered design comprising a plurality of stacked stiffness blocks. The design, which could be formed as an integral component, can be made as open for cutting techniques. The stiffness unit 20 could thus be continuously 3D-printed component without the gap, and the material could then be removed from the gap and other sections. This type of design could also provide for thicker walls of the unit 20.

Figure 7:
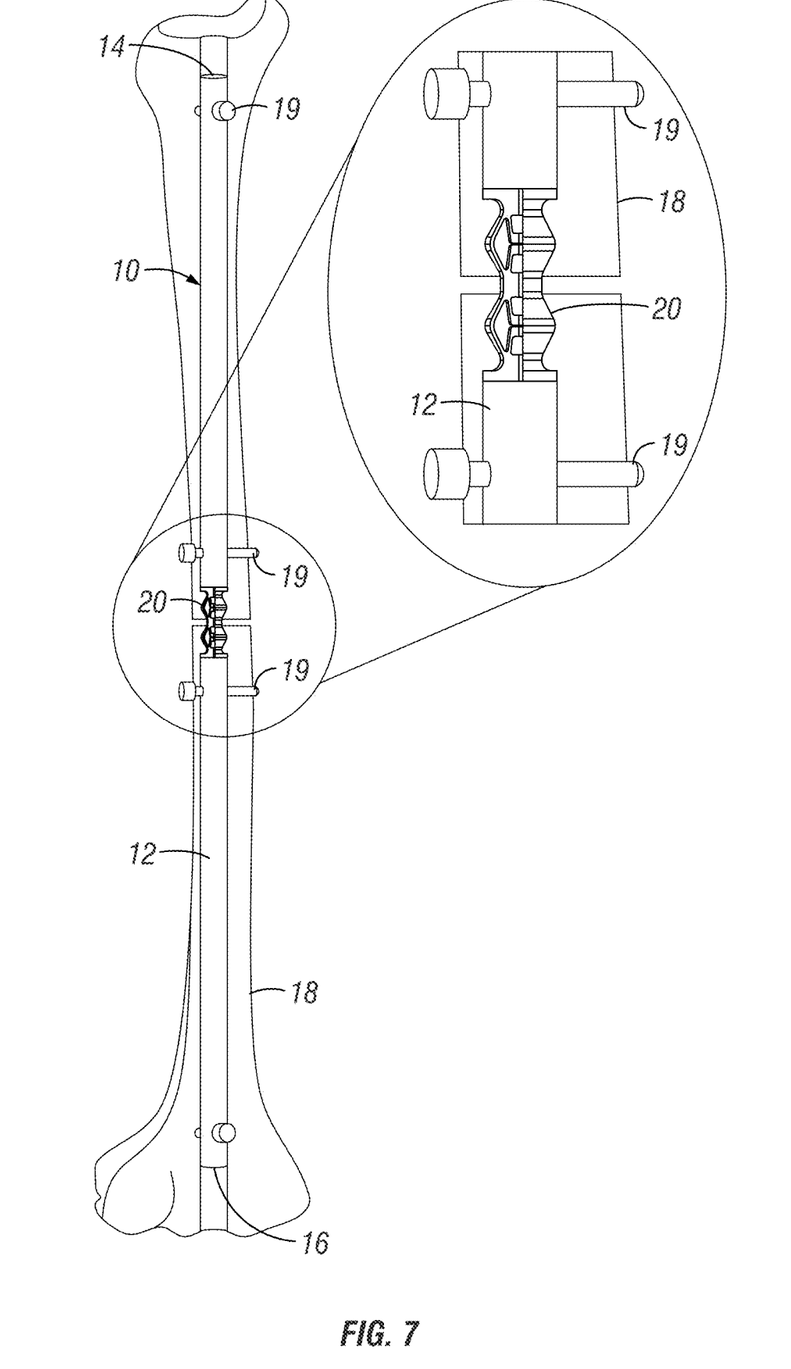
FIG. 7 is a view with an enlargement of a tunable stiffness bone rod depicted in a fractured bone.
Figure 8A:
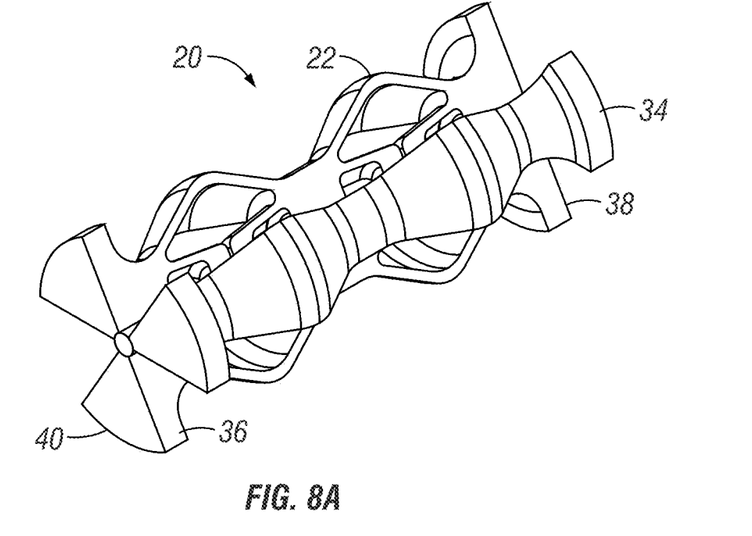
FIG. 8A-8C show various embodiments of a tunable stiffness unit according to aspects of the disclosure.
Figure 8B:
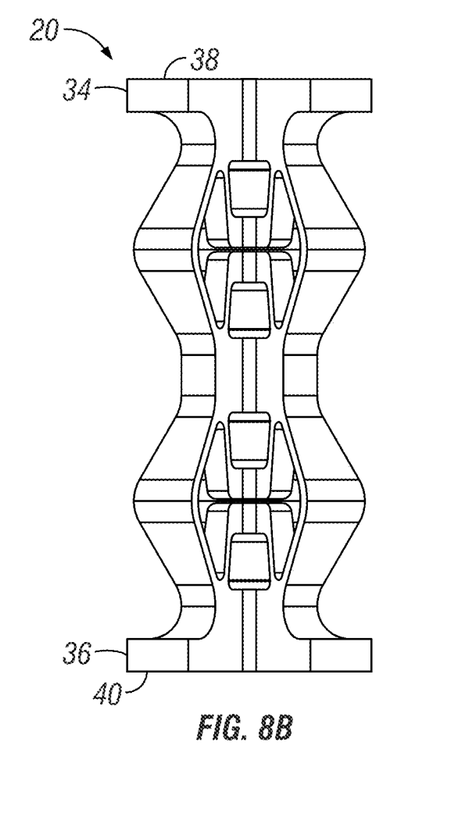
Figure 8C:
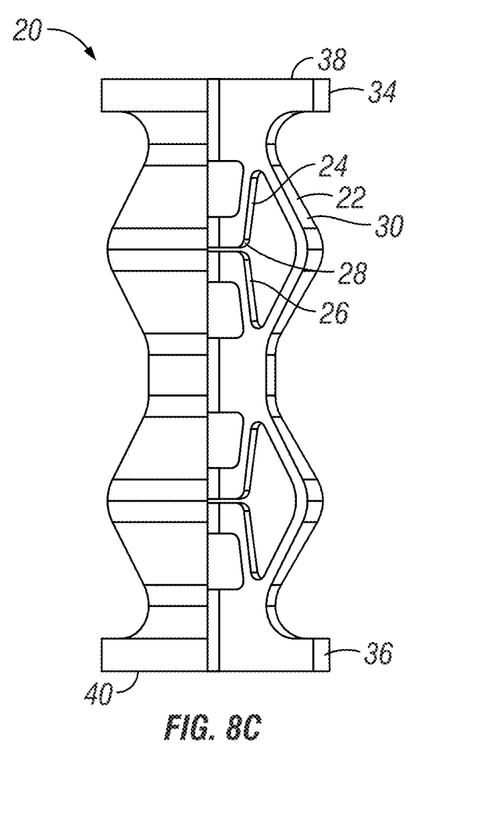

As noted, FIG. 7 shows an exemplary tunable stiffness bone rod 10 inside an exemplary fractured tibia. FIGS. 8A-8C show various views of a tunable stiffness unit 20 comprising two hexagonal cells 32. As mentioned, the design such as shown in FIGS. 8A-8C could be considered a partially revolved stiffness block comprising two hexagonal cells, or could be considered a stacked unit comprising a cluster of radially spaced and stacked stiffness blocks.

Next, the design optimization for the stiffness unit needed clarification. Different objective functions were proposed and tried for optimization. Two objective functions were used to optimize the design parameters, the first one having to do with curve characteristics, force-displacement behavior, and the second one having to do with elasticity measures.

Referring to FIG. 6, one design parameter, the half gap size "AA" was fixed according to the fracture gap length to make sure that the rod behavior changes precisely after an absolute relative displacement of the fractured part of the bone. The optimum normal strain for bone growth by the osteoblast cells is about 9%. For instance, if the patient's fracture gap is 3-mm, the optimum compression in the fracture region should be about 0.27-mm. If the designed bone rod has two hexagonal cells aligned vertically, the total gap size inside each hex cell should be equal to about 0.135-mm since both of them are normally operating in the elastic region of the material before their gap closures. Therefore, nine remaining dimensional parameters, BB, CC, DD, EE, FF, GG, R1, R2, and R3, were the design variables in the optimization process.

The ratio of the maximum slope of the force-displacement curve to its respective minimum was considered as the first objective function, as shown in Eq. 1 below. However, the negative value of the ratio was computed to utilize optimization algorithms looking for minima of objective functions readily. As the explicit finite element (FE) simulations may involve some computational noises in the response, and the negative slope in the force-displacement curve does not have physical meaning, the negative slope values were ignored. Furthermore, twenty equally spaced time intervals were considered in the FE process to get a simulated response with twenty line segments with sufficient accuracy. This form of objective function dictates that design schemes showing more significant changes in their elastic behavior after the gap closure is more favorable in the optimization process.

$$\vec{d} = (AA = a * \text{fracture\_gap}, BB, CC, DD, EE, FF, GG, R1, R2, R3)$$

$$OF_1(\vec{d}) = - \max_{1 \le i \le N_t} \{Slope_{Force-Disp}(\vec{d}, t(i)) > 0\} \Big/ \max_{1 \le i \le N_t} \{Slope_{Force-Disp}(\vec{d}, t(i)) > 0\} \quad (1)$$

In Eq. (1), $\vec{d}$ is the vector of design variables, and $\alpha$ *fracture_gap is the value of parameter AA as discussed before. $OF_1$ is the first objective function of design variables ($\vec{d}$), $N_t$ is the number of time steps of FE results, which contain the value of field outputs such as displacements and reaction forces, $Slope_{Force-Disp}$ is the slope of the force-displacement curve of a specific design ($\vec{d}$) determined at a specific time step of FE solution (t(i)), which is proportional to the total displacement imposed on the model.

The second objective was avoiding any plastic deformation, which would change the mechanical response permanently. Satisfying such a condition was first implemented by considering only the first objective and assigning an extreme value to this objective whenever the response of the structure surpasses the maximum allowable stress, which is the yield stress of the material. Single-objective optimization did not produce favorable results regardless of the optimization method used and its hyperparameters because better compliance with the objective curve points demands higher maximum Mises stress, especially in the surrounding arms with a thin layer of the material. Thus, a multi-objective optimization method was chosen to satisfy all design criteria simultaneously. Therefore, the maximum Mises stress in the whole design domain was considered as the second objective because the metallic materials used for the implants are mostly ductile. Only elastic behavior of the material was defined for the material properties in the FE simulation as we were only interested in elastic designs that show stress levels lower than the yield limit of the material. Accordingly, the maximum Mises stress for every design scheme was extracted at the maximum possible force, proportional to the patient's weight, imposed on the fractured bone. It is formulated in Eq. 2 with $OF_2$ as the second objective function of the optimization problem, $N_{el}$ as the number of FE model elements, $\sigma_{Mises}$ as the Mises stress, t as the time step, RF(t) as the reaction force of the model due to compression, and β *Weight as a fixed multiplier of patient's weight. β was considered 1.3, as a medium value according to previous studies, which posit increasing loading levels with the time of bone healing.

$$OF_2(\vec{d}) = \max_{1 \leq i \leq N_{el}} \{\sigma_{Mises}(\vec{d}, t, element_i) \mid RF(t) \leq \beta * \text{Weight}\} \quad (2)$$

FE modeling was performed to quantify the mechanical behavior of each design scheme in the optimization loop and compare it with the desired response of the structure. The FE analyses were done in the commercial software package of ABAQUS using mm, N, and tonne/m3 units for dimensions, forces, and densities, respectively. Simple elastic behavior was considered for material properties. Hard contact behavior was also defined in the gap area to simulate the contact behavior. All boundary conditions were defined as displacements for faster convergence. Therefore, the reaction force of the model in the direction of displacement was the output of the simulation. In the reversed case of force (pressure) loading, the output was model displacement.

Figure 10:
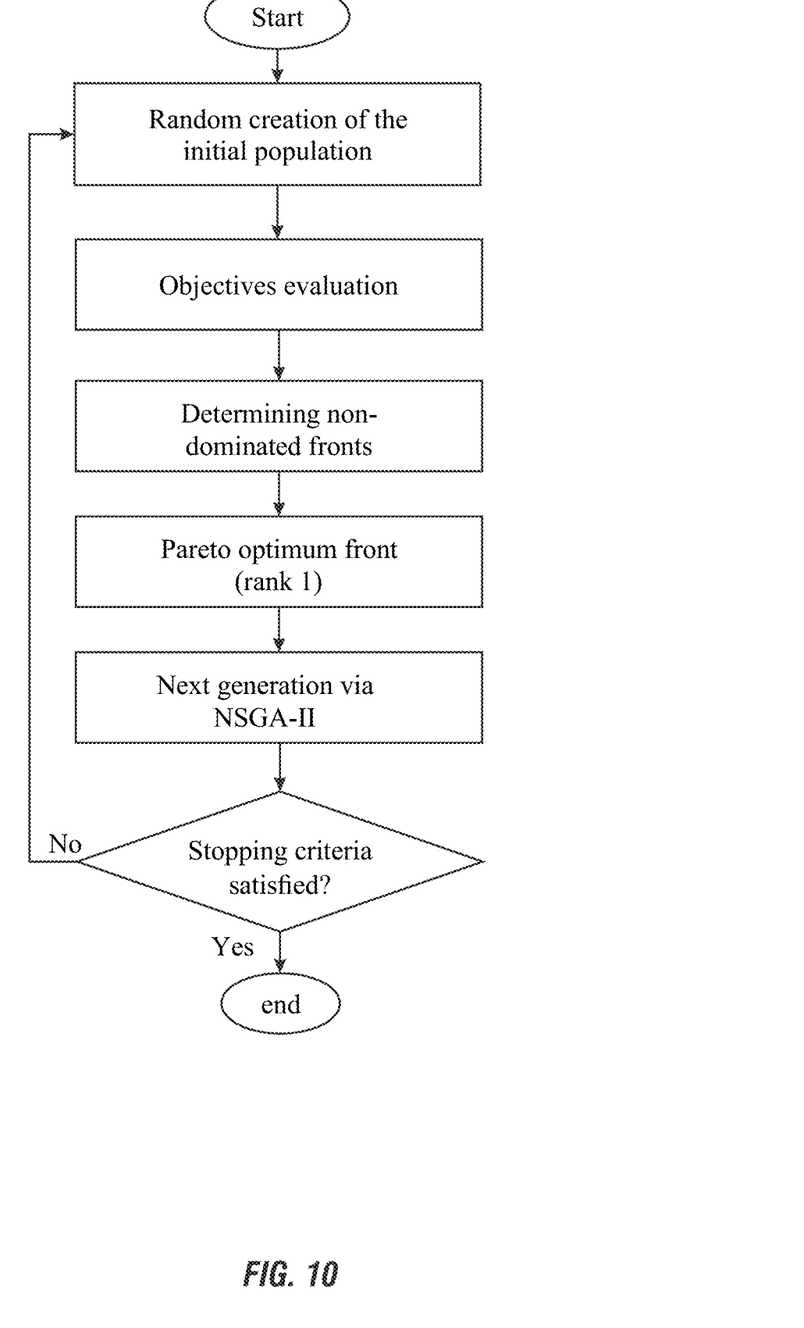
FIG. 10 is flow diagram showing the steps of a Genetic Algorithm for use with aspects of the present disclosure.

As the smooth behavior of the aforementioned objective functions has not been guaranteed, and finding the global extrema was desired in this study, the stochastic method of Genetic Algorithm (GA) for multi-objective functions was chosen for the optimization, a variant of NSGA-II as a controlled, elitist genetic algorithm. The flowchart of the algorithm is shown in FIG. 10. The algorithm tries to find a non-dominated population of the design schemes. The Pareto front would illustrate such a population in the design variable space or the objective one as requested in the software. The objective variable space was more suitable to track the optimization process since it was 2D. The best point is the one showing the minimum values for the negative slope ratio of the force-displacement curve as well as maximum Mises stress in the FE simulation. However, these two have a reverse relationship, as shown in the Pareto fronts of optimization trials. The essential stopping criteria of NSGA-II is the spread quantity as a measure of Pareto set movement. Iterations will stop if the spread value change falls below a specific threshold while being less than an average of spreads in previous generations. Other stopping criteria are the maximum number of iterations as well as a pre-determined set of threshold objectives. The threshold values were defined so that the optimization algorithm could stop searching for better design schemes if the first and second objectives were less than −10 as the negative slope ratio and the yield stress of the material, respectively. As a case study, the input data for modeling and design optimization were defined as presented in Table 1 for a 70 kg patient with β=1.3, and the last Pareto front was subsequently obtained. The applied load on the model is higher than β *Weight since stiffness change may occur in different load levels. "r" is the radius of a cylinder connecting the three revolved sections of the bone rod as shown in FIG. 8. The best point of the front, for which the design parameters are presented in Table 2, was also determined based on the constraint on the maximum allowable Mises stress (objective 2).

TABLE 1

Input data of optimization

| D/2 (mm) | r (mm) | AA (mm) | Applied load (N) | Stiffness (MPa) | Poisson's ratio | Yield Stress (MPa) |
|---|---|---|---|---|---|---|
| 4 | 0.25 | 0.075 | 2100 | 200000 | 0.27 | 1250 |

TABLE 2

Dimensional parameters of the best point in the Preto front (unit: mm)

| BB | CC | DD | EE | FF | GG | R1 | R2 | R3 |
|---|---|---|---|---|---|---|---|---|
| 1.615 | 0.883 | 1.975 | 1.084 | 1.691 | 0.655 | 0.314 | 0.507 | 0.715 |

As disclosed, at least some aspects and/or embodiments of the tunable bone rod 10 as disclosed herein are made by additive manufacturing. Powder Bed Fusion is a metal AM process category utilizing a thermal energy source that selectively sinters (i.e., without melting to the point of liquefaction) or fuses regions of a thin powder layer. Selective laser sintering (SLS) as the first PBF method was later developed into Selective Laser Melting (SLM) and Electron Beam Melting (EBM), which entirely melt small regions of metal powder called "melt pool" resulting in better mechanical properties than sintering method, due to technological and power source improvement. A thin layer of metal powder (typically between 30-50 μm) deposited on a flat substrate via a powder deposition system is locally molten along a predefined path to make the first layer of the part. Then, the substrate is lowered for a new powder layer to be deposited and transformed into the next slice of the part. This process will continue to reach the final slice of the part.

According to an exemplary embodiment including any of the aspects of the tunable bone rod disclosed herein, the bone rod can be formed with a metal 3D printer. An exemplary metal 3D printer is a 3D Systems ProX300, which utilizes fine steel powder (Stainless Steel 17-4 PH acquired from 3D Systems) for the build material and a 500-watt laser to melt the powder into the required geometry. The printer has a 250 mm×250 mm build area, which is sufficient for 3D printing of the hexagonal cells of a complete bone rod. Having a compacting carbide roller, it increases material density and allows for larger overhangs, completely unsupported material, where the geometry allows. It is especially useful when the cost of the whole manufacturing process and the effect of support material on the quality of the end product and on the complexity of removing them are taken into account.

Figure 9:
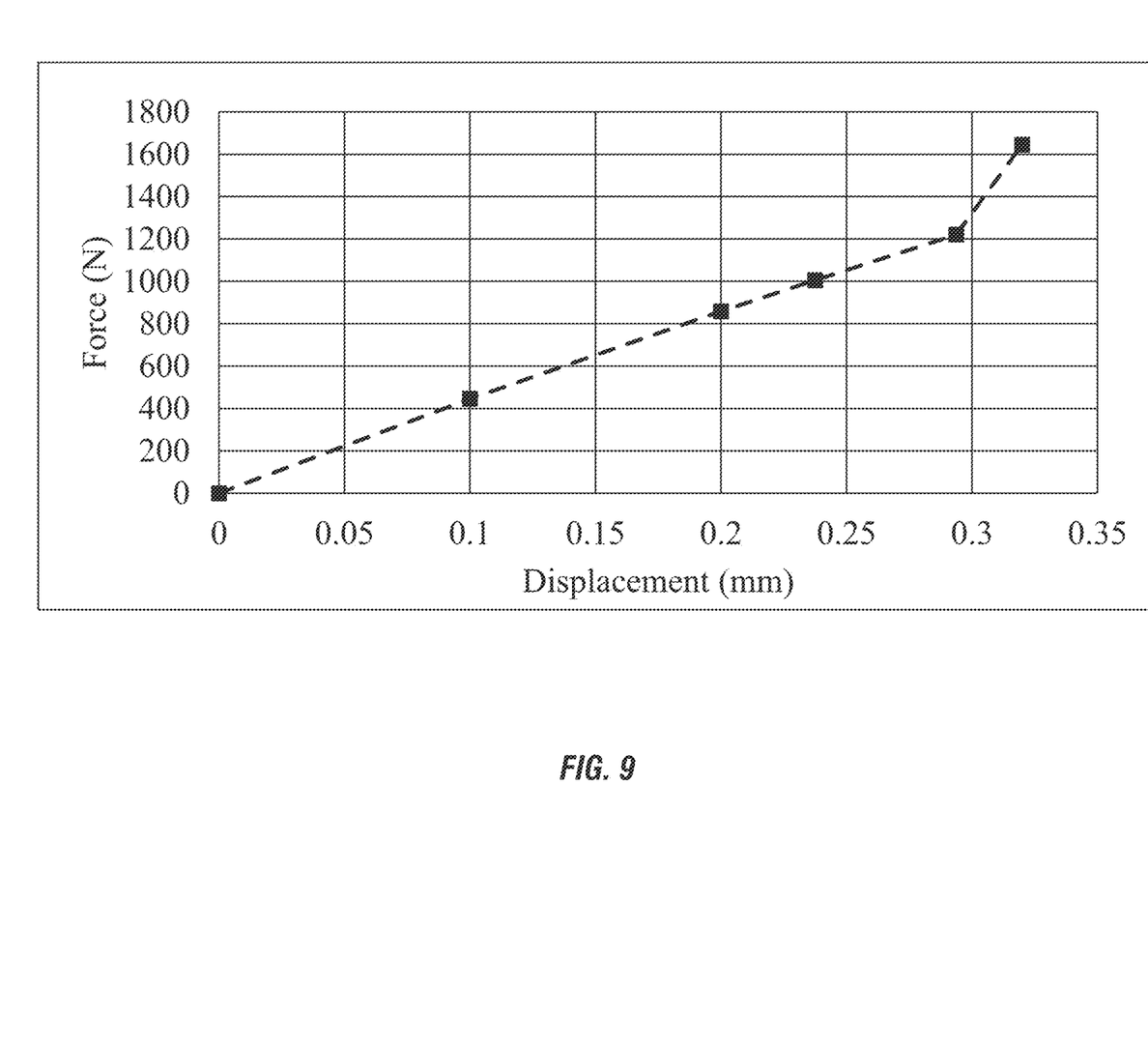
FIG. 9 is a table showing force vs. displacement curve due to axial load over an exemplary stiffness unit.

A compression test can be done as well. An exemplary compression test can utilize an Instron machine with a 20 kN load cell, and ASTM E9-19 standard method for compression testing of metallic materials at room temperature. The effective stiffness ratio was about 2, according to the experimental results presented in the graph shown in FIG. 9.

Therefore, the present disclosure has shown and described aspects and embodiments for a novel tunable stiffness bone rod for healing tibia bone fractures. Upon applying axial force, the bone rod deforms with low stiffness, and it becomes stiffer when the embedded gap gets closed. Considering the additive manufacturing (AM) limitations, the patient-specific designs can be obtained using multi-objective Genetic Algorithm (GA) optimization in conjunction with FE modeling for calculating the objective functions, ensuring reversible and controlled elastic deformation. Such novel bone rods allow the broken bone to move in a controlled fashion along the longitudinal axis, and this motion stimulates bone healing while it prevents the common stress-shielding of ordinary bone rods, which leads to osteoporosis. Taking advantage of the flexible AM technique, the designed bone rods can be 3D printed with the FDA approved material, stainless steel. The developed design framework and AM together offer optimum bone rods given patient weight, fracture gap, and selected building material.

It should be appreciated that the invention can include any combination of any of the aspects of any of the embodiments disclosed. In addition, it should be apparent to those skilled in the art that variations, alternatives, and changes that do not affect the scope of the covered application and appending claims are to be covered and considered a part of the invention.

The invention claimed is:

1. A tunable bone rod, comprising:
   an elongated rod having a diameter and being separated into upper and lower portions, the elongated rod adapted for an interior portion of a long bone, such as a femur, tibia, fibula, humerus, radius, and ulna;
   a tunable stiffness unit positioned axially along the longitudinal length of the elongated rod between upper and lower portions, said tunable stiffness unit comprising:
      a plurality of stiffness blocks around a common, longitudinal axis of the bone rod, each of the stiffness blocks comprising an upper flex member having an upper flange and a lower flex member having a lower flange with the upper and lower flex members separated by a gap, and a support arm connected to the upper and lower flex members, wherein said upper and lower flex members are movable to contact one another under axial load in a linear direction;
   wherein said tunable stiffness unit includes a bilinear load response to the axial load applied in the linear direction; and
   wherein said tunable stiffness unit is symmetrical about a longitudinal axis of the unit; and
   wherein said tunable stiffness unit has a width at or within the diameter of the elongated rod.

2. The tunable bone rod of claim 1, wherein the upper and lower flex members and the support arm comprise a hexagonal shape.

3. The tunable bone rod of claim 2, wherein the hexagonal shape comprises an irregular hexagon.

4. The tunable bone rod of claim 1, wherein the stiffness unit further comprises an upper stiffness block and a lower stiffness block positioned in axial relationship along the length of the elongated rod.

5. The tunable bone rod of claim 4, wherein the plurality of stiffness blocks forms a non-continuous, partially revolved member.

6. The tunable bone rod of claim 5, wherein the plurality of stiffness blocks comprises three stiffness blocks used together.

7. The tunable bone rod of claim 1, wherein the tunable bone rod comprises stainless steel.

8. The tunable bone rod of claim 1, wherein the stiffness unit deforms upon application of axial force with low stiffness, and becomes stiffer when the gap between the upper member and lower member closes.

9. A tunable stiffness block for use in aiding the healing of a fracture of a long bone, such as a femur, tibia, fibula, humerus, radius, and ulna, comprising:
   an upper block body having an upper flange;
   a lower block body having a lower flange;
   a support arm connecting the upper and lower block bodies to form a hexagonal cavity between the upper and lower block bodies, wherein a gap is formed between the upper and lower block bodies;
   wherein the support arm flexes to close the gap between the upper and lower block bodies under an axial load in a linear direction; and
   wherein said tunable stiffness block includes a bilinear load response to the axial load applied in the linear direction;
   said tunable stiffness block designed according to a patient's weight, fracture gap, and material of the tunable stiffness block; and
   wherein the upper and lower flanges have a width being measured perpendicular to an elongated height of the tunable stiffness block and the support arm extends outwardly and within the width of the upper and lower flanges.

10. The tunable stiffness block of claim 9, wherein the upper and lower block bodies are substantially symmetrical.

11. The tunable stiffness block of claim 9, wherein the hexagonal cavity comprises an irregular hexagon shape.

12. A tunable stiffness unit for use in aiding the healing of a fracture of a long bone, such as a femur, tibia, fibula, humerus, radius, and ulna, comprising:
   a plurality of tunable stiffness blocks around a common, longitudinal axis of a bone rod, each of the tunable stiffness blocks comprising an upper block body having an upper flange, a lower block body having a lower flange, and a support arm connecting the upper and lower block bodies to form a hexagonal cavity between the upper and lower block bodies, wherein a gap is formed between the upper and lower block bodies;
   wherein the support arm flexes to close the gap between the upper and lower block bodies under an axial load in a linear direction;
   wherein said tunable stiffness unit includes a bilinear load response to the axial load applied in the linear direction;
   wherein the plurality of tunable stiffness blocks are oriented radially with a radial gap between corresponding stiffness blocks;
   wherein said tunable stiffness unit is symmetrical about a longitudinal axis of the unit;

wherein the bone rod comprises an elongated rod having a diameter and being separated into upper and lower portions; and wherein said tunable stiffness unit has a width that is at or within a diameter of the bone rod.

13. The tunable stiffness unit of claim 12, wherein the plurality of tunable stiffness blocks comprises two or more stiffness blocks stacked longitudinally.

14. The tunable stiffness unit of claim 13, wherein the plurality of tunable stiffness blocks comprises three sets of two longitudinally stacked stiffness blocks radially spaced.

15. The tunable stiffness unit of claim 12, wherein the plurality of stiffness blocks comprise stainless steel.

16. The tunable stiffness unit of claim 12, wherein the gap is sized to be approximately 9% of a bone fracture gap.

* * * * *